(12) United States Patent
Rinker et al.

(10) Patent No.: US 9,781,952 B2
(45) Date of Patent: Oct. 10, 2017

(54) SMOKELESS CIGARETTE SUBSTITUTE PRODUCT (75) Inventors: Arno Rinker, Hamburg (DE); Philipp Litzenberger, Hamburg (DE)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 1245 days.

(21) Appl. No.: 13/384,639

(22) PCT Filed: Jul. 22, 2010

(86) PCT No.: PCT/EP2010/060649
§ 371 (c)(1),
(2), (4) Date: Jan. 18, 2012

(87) PCT Pub. No.: WO2011/009920
PCT Pub. Date: Jan. 27, 2011

(65) Prior Publication Data
US 2012/0111346 A1    May 10, 2012

(30) Foreign Application Priority Data

Jul. 22, 2009 (EP) .................................. 09 166 122
Jul. 22, 2009 (EP) .................................. 09 166 153

(51) Int. Cl.
*A24F 47/00* (2006.01)
*A61M 15/06* (2006.01)
(Continued)

(52) U.S. Cl.
CPC .......... *A24F 47/002* (2013.01); *A24F 47/008* (2013.01); *A61M 11/003* (2014.02);
(Continued)

(58) Field of Classification Search
None
See application file for complete search history.

(56) References Cited

U.S. PATENT DOCUMENTS 3,672,568 A  *  6/1972  Foote ........................ F24H 1/00
                                                         236/44 R
4,083,372 A      4/1978  Boden
                (Continued)

FOREIGN PATENT DOCUMENTS

AT         414084 B     6/2006
DE        2939965 A1    4/1980
              (Continued)

OTHER PUBLICATIONS

Office Action dated Apr. 2, 2014 in Japanese Patent Application No. 2012-521043 (with English language translation).
(Continued)

*Primary Examiner* — Michael J Felton
(74) *Attorney, Agent, or Firm* — Oblon, McClelland, Maier & Neustadt, L.L.P.

(57) ABSTRACT

A method and device are provided for volatilizing active and/or aroma materials for releasing an inhalable aerosol, wherein a fluid flows through a flow channel in a preferably cylindrical hollow body, wherein the fluid in the flow channel entirely or in part flows through at least one vaporizer membrane in a fluid stream, wherein the at least one vaporizer membrane has been and/or is wetted with a substance containing an active and/or aroma material to be vaporized, and wherein the fluid additionally contains thermal energy and vaporizes the substance on flowing through the vaporizer membrane and supplies the vaporized substance to the fluid stream.

21 Claims, 4 Drawing Sheets

(51) Int. Cl.
*A61M 11/00* (2006.01)
*A61M 11/04* (2006.01)
*A61M 16/10* (2006.01)

(52) U.S. Cl.
CPC .......... *A61M 11/045* (2014.02); *A61M 15/06* (2013.01); *A61M 16/107* (2014.02); *A61M 11/042* (2014.02); *A61M 2202/0468* (2013.01)

(56) References Cited

U.S. PATENT DOCUMENTS

| | | | | |
|---|---|---|---|---|
| 5,800,741 | A * | 9/1998 | Glenn | F24F 6/04 261/107 |
| 2006/0174901 | A1* | 8/2006 | Karles | A24D 3/163 131/337 |
| 2008/0241255 | A1 | 10/2008 | Rose | |
| 2011/0036346 | A1* | 2/2011 | Cohen | A61M 15/0065 128/200.14 |

FOREIGN PATENT DOCUMENTS

| | | |
|---|---|---|
| DE | 4030257 A1 | 4/1992 |
| DE | 69130682 T3 | 7/2004 |
| DE | 202005006312 U1 | 12/2005 |
| DE | 202006001633 U1 | 6/2006 |
| DE | 202006001663 U1 | 6/2006 |
| DE | 10 2007 043 776 A1 | 3/2009 |
| EP | 430559 B1 | 6/1991 |
| EP | 0430559 B1 | 6/1991 |
| WO | 9836651 A1 | 8/1998 |
| WO | 2005099494 A1 | 10/2005 |
| WO | 2008113420 A1 | 9/2008 |

OTHER PUBLICATIONS

International Search Report dated Oct. 21, 2010 in PCT/EP2010/060649.
International Search Report PCT/EP2010/060649; dated Oct. 21, 2010.

* cited by examiner

SMOKELESS CIGARETTE SUBSTITUTE PRODUCT

TECHNICAL FIELD

The present invention relates in general to a method and a device for smoke-free inhalation of nicotine and/or additives.

BRIEF DISCUSSION OF RELATED ART

When a conventional cigarette is smoked, tobacco is burned and the smoke arising during this combustion is inhaled (mainstream smoke) or discharged into the surrounding environment (sidestream smoke).

Mainstream smoke is the crucial factor in damaging the health of the consumer, but is what gives him/her the desired pleasure. Sidestream smoke is the crucial factor in damaging the health of passive smokers and is desired neither by the passive smokers nor by the consumer.

Over 4800 different substances have been identified in cigarette smoke, of which around 70 are demonstrably carcinogenic.

The aim of methods and devices based thereon for smoke-free inhalation of nicotine and/or additives is to offer the consumer a substitute for the conventional cigarette which causes significantly less harm to the consumer and third parties, preferably no harm at all to the consumer and third parties, while however retaining the consumer experience of a conventional cigarette.

Known methods and devices describe a plurality of possibilities for atomising, evaporating or vaporising a substance, preferably a mixture of nicotine and additives, in order to produce an inhalable aerosol which, on inhalation, is intended to offer the consumer a consumer experience which is as identical as possible in pharmacological and organoleptic terms to the smoke from a conventional cigarette.

Methods and devices, such as for example compressible atomisers described in WO 98/36651, which are based solely on the principle of atomising a substance, have the crucial drawback due to the underlying principle that while it is indeed straightforwardly possible to produce an aerosol with an adequate pharmacological effect, as a result of the cold fluid and the concomitant supersaturation the substance accordingly condenses prematurely, whereby the consumer's lips and oral cavity are wetted, which has a strongly negative impact on the organoleptic experience with regard to the required equivalence to the consumer experience of smoking a conventional cigarette.

In known methods and devices which evaporate or vaporise a substance, depending on the vapour pressure of the substance, the latter is either passively evaporated solely by a fluid stream or is actively vaporised by the additional input of for example thermal energy.

On evaporation, the substance passes from the liquid to gaseous state at below the boiling temperature. At the particulate level, this means that individual particles may dissociate from the liquid even far below the boiling temperature. However, in comparison with vaporisation, this proceeds only very slowly.

The following methods and devices operate according to the principle of evaporation:

AT414084BB describes for example a cardboard tube made of paperboard or biodegradable plastics, which in a further development is air-impermeably coated on the inside by an aluminium foil or plastics film. A supporting body arranged within this tube in the form of for example stair-step slats brings a fluid stream flowing through the device into contact with a substance which is in this manner introduced into the fluid stream by evaporation.

DE202005006312U1 describes a plastics tube with a predetermined bending point and an internal porous or hollow impregnation body which is preferably cylindrical and for example made of cotton. This impregnation body is intended to release a substance to a fluid stream by evaporation.

U.S. Pat. No. 4,083,372 describes a cigarette-simulating inhaler, wherein a substance to be evaporated is stored in an elastic capsule at the mouth end of a tube and a wick extends over the remaining length of the tube. Immediately before consumption, the capsule is destroyed by puncturing and the substance is completely absorbed by said wick. On drawing on the tube, the substance is then evaporated from the wick.

DE202006001663U1 describes a two-part cigarette tube of plastics, paper or metal in which a cushion impregnated with a substance is located between two diaphragm valves, wherein the diaphragm valves are opened by a fluid stream and the cushion consequently releases the substance into the fluid stream by evaporation.

DE2939965C2 likewise describes a tube in which a cushion to which a substance has been applied is arranged in a fluid stream in such a manner that a venturi channel is formed by the surface of the cushion, wherein the reduced pressure consequently generated by a fluid stream assists evaporation.

DE69130682T3 describes a cartridge for a nicotine inhaler consisting of a copolymer housing sleeve and, contained therein, a nicotine container which preferably takes the form of a porous polymer plug which, when a fluid stream flows through, releases nicotine to said fluid stream by evaporation. This invention is currently distributed as the "Nicorette Inhaler".

A feature common to the previously described inventions is that, because additional input of thermal energy has been dispensed with, they are not capable of forming sufficient quantities of aerosol in the case of a fluid stream of a volume of the order of 35 ml in 2 seconds at a reduced pressure of roughly 0.5 kPa-1.5 kPa, as is usually generated by a consumer when drawing on a conventional cigarette, in order to offer a pharmacological consumer experience which is equivalent to smoking a conventional cigarette.

Due to the enthalpy of vaporisation of pure nicotine, which in comparison with all nicotine salts has the lowest enthalpy of vaporisation, it is not possible, even with the assistance of solvents, to achieve a nicotine concentration of the order of magnitude of 0.05-0.1 mg per draw without input of additional energy, for which reason methods and devices without additional input of thermal energy are not generally well accepted by consumers.

In order to disguise such an inadequate pharmacological effect due to the underlying principle, most methods and devices contain a substance which itself contains menthol, since menthol has a very low enthalpy of vaporisation, whereby the consumer is at least offered an organoleptic inhalation experience even without input of thermal energy.

Since, for the above-stated reasons, it is not possible to provide a product which is a complete substitute for a cigarette and is solely based on evaporation, i.e. without input of energy of vaporisation, a number of methods and devices have been developed which supply energy either to the fluid stream or to the substance itself, which is to be converted into an aerosol, whereby the latter is vaporised.

WO2005/099494A1 describes a device for smoke-free inhalation of nicotine, wherein a nicotine-containing substance is stored in a nonwoven cushion and released to an ultrasonic vaporiser for vaporisation. This product is distributed by various suppliers as the "e-cigarette".

EP 0430559 B1 describes a device which, by means of an electrical heating device which is in contact with an aroma medium, releases a predetermined quantity of substance containing aroma material to the consumer. This is achieved by purposeful electronic control of the heating unit.

WO 2008/113420 A1 describes a smoke-free substitute cigarette product which uses the hot combustion waste gas from a premix burner to produce the desired inhalable aerosol by vaporisation from a nicotine aroma material depot.

A feature common to all known methods and devices for smoke-free inhalation of nicotine and/or additives which are based on the principle of evaporation or vaporisation of a substance is that the particular substance is stored in a three-dimensionally shaped medium, preferably a single or multipart cushion or cylindrical absorbent and/or porous body, wherein these three-dimensionally shaped media also act, in addition to performing their storage function, as an evaporator or vaporiser by having a fluid flow through and/or around them and optionally by direct and/or indirect input of thermal energy or discharge the substance contained therein to an additional evaporator or vaporiser device.

Drawbacks of all known methods and devices for smoke-free inhalation of nicotine and/or additives which supply the substance to an external evaporator or vaporiser device are on the one hand the associated undesired contamination of the evaporator or vaporiser device, as is known from "e-cigarettes" (WO2005/099494A1), and on the other hand the meterability of the substance, whereby the evaporator or vaporiser device, inter alia depending on its particular spatial location, is frequently either oversupplied or undersupplied.

A drawback of all known methods and devices which also utilise the storage medium as evaporator or vaporiser is inadequate efficiency of the evaporator or vaporiser function, whereby enrichment of the fluid stream with a desired substance cannot be achieved to the desired extent or requires an unnecessarily high direct and/or indirect input of thermal energy.

A further drawback of all known methods and devices which also utilise the storage medium as a vaporiser, is frequently a decline in the intensity of vaporisation as the consumption period progresses, since as vaporisation progresses the saturation of the storage medium and thus the saturation of the vaporiser inevitably falls.

The stated drawbacks mean all known methods and devices for smoke-free inhalation of nicotine and/or additives offer the consumer either an excessively weak and/or excessively non-uniform inhalation experience or an inhalation experience which, while sufficiently strong and/or uniform, involves excessive technical complexity and/or energy input.

BRIEF SUMMARY

The invention provides a method and a device based thereon for smoke-free inhalation of nicotine and/or additives, which permits vaporisation of nicotine and/or additives with distinctly increased efficiency relative to the prior art and preferably simultaneously permits uniform release of nicotine and/or additives over the complete consumption cycle.

The invention provides a method for volatilising active and/or aroma materials for the purpose of releasing an inhalable aerosol, wherein a fluid which has been exposed to thermal energy flows through a flow channel in a preferably cylindrical hollow body and wherein the fluid in this flow channel entirely or in part flows through at least one vaporiser membrane, wherein the at least one vaporiser membrane has been and/or is wetted with a substance containing an active and/or aroma material and wherein the fluid additionally containing thermal energy, i.e. which has been exposed to thermal energy, vaporises this substance or substances on flowing through the vaporiser membrane and supplies it to the fluid stream.

A membrane for the purposes of the invention is a fluid-permeable two-dimensional structure, such as for example a laid fabric, warp knitted fabric or weft knitted fabric made from fibres, wherein permeable membranes are those membranes which allow the fluid stream to pass through completely while selectively permeable or semipermeable membranes are those membranes which remove particles of a specific size from the fluid stream.

For the purposes of the present invention, a "fluid containing thermal energy" or a "fluid which has been exposed to thermal energy" is taken to mean a fluid to which thermal energy has been supplied prior to passage through the vaporiser membrane, i.e. the temperature of which is above ambient temperature, preferably amounting to at least 60° C., advantageously to at least 80° C., before the membrane (i.e. before the vaporisation of active and/or aroma materials). In general, the input of heat is controlled such that the temperature of the fluid preferably does not exceed 160° C., particularly preferably 140° C. It should be noted in this connection that the generation of the energy of vaporisation is not itself a subject matter of the present invention.

Such a method, preferably for inhaling a nicotine-aroma mixture, is made possible by the arrangement of at least one substance, preferably containing nicotine and/or aromas, to be vaporised on at least one permeable vaporiser membrane in a fluid stream, wherein it is possible by this method to achieve a very large ratio of fluid-substance contact area to vaporiser mass (membrane mass) with a simultaneously low flow resistance. The advantage of such a method, in contrast with the method in which a substance, preferably containing nicotine and/or aromas, to be vaporised is applied onto a three-dimensionally shaped medium, for example a cushion or a cylindrical absorbent and/or porous body, is that the efficiency on vaporisation, i.e. the ratio of nicotine input to nicotine output, is higher due to the underlying principle.

In further developments of the invention, one or more filter elements may be provided both upstream and preferably downstream in order to remove undesired substances from the fluid. These preferably comprise filter membranes which either retain these undesired substances or convert them into harmless substances.

In a further development, the method accordingly comprises the use of at least one filter membrane, wherein the filter membrane is selectively permeable, i.e. is not permeable to all substances, in order purposefully to remove undesired substances, such as for example particles, from the fluid stream without unnecessarily increasing flow resistance. The advantage of such a development resides in the possibility, for example by arrangement after a vaporiser membrane, of removing from the fluid stream any unvaporised constituents of the substance to be vaporised which have been entrained by the fluid stream or, by using the method in combination with a fluid-heating method, of removing any undesired substances produced thereby. An arrangement before a vaporiser membrane or a combined arrangement before and after a vaporiser membrane are explicitly also provided. This is for example the case when a plurality of vaporiser membranes are arranged in the flow channel, wherein each is provided for vaporising substances containing different active and/or aroma materials, but the filter function is intended to be limited to one or several of these substances.

Alternatively or additionally, at least one filter membrane is provided with a catalyst material which breaks down any harmful constituents of the fluid stream which may be present into constituents which are not harmful to health.

The advantages of such a method reside on the one hand in the possibility of purposefully enriching a fluid stream with desired substances and on the other hand of removing undesired substances therefrom with elevated efficiency and low flow resistance.

The above-stated membrane or membranes, i.e. both vaporiser membrane(s) and/or filter membrane(s), may also themselves comprise single or multilayer membrane(s), permeable or semipermeable membranes or contain combinations thereof. The membranes comprise known materials, for example of nonwoven fabrics, woven fabrics, weft knitted fabrics and/or warp knitted fabrics. Nonwoven fabrics made from regenerated cellulose fibres are preferably used as the material for vaporiser membranes, while nonwoven fabrics made from Manila hemp fibres are particularly suitable for filter membranes.

The membranes usable according to the invention may be arranged orthogonally and/or at an angle to the fluid stream, wherein three-dimensional topologies or structures (for example hollow cones, pleats) may also be provided. In the case of the vaporiser membrane, it is important that it permits the greatest possible contact with the fluid as the latter flows through. Due to the underlying principle, it is naturally important for a filter membrane that the fluid stream substantially flows through it.

In a further preferred development, the vaporiser membrane(s) are supplied with liquid to be vaporised via capillaries from at least one cavity, preferably filled with a storage medium, for example a foam or nonwoven fabric, via supply orifices in the cavity wall. In this manner, the vaporiser function may be decoupled from the storage function.

The advantage of this development make it possible to ensure constantly optimum wetting of the vaporiser membrane(s) while simultaneously ensuring an optimum quantity, adjustable in accordance with the consumer's wishes, of substance to be vaporised per act of consumption, if the storage medium is able to absorb a multiple of the volume of substance relative to the vaporiser membrane. In this way, uniform vaporisation over a number of draws is ensured without the technical complexity of selectively heatable multichamber systems.

A further advantage of this variant is that active and/or aroma materials, for example nicotine and/or other additives, are protected from atmospheric influences until they are consumed, so achieving the longest possible storage life. It may moreover also be ensured thereby that substances with relatively different volatilities are available in the intended combination during consumption.

In a further preferred development the cavity (cavities) comprises (comprise) at least one additional pressure equalisation orifice in the cavity wall, whereby the cavity is in connection with the flow channel and/or the atmosphere, whereby pressure equalisation is ensured on discharge of the substance to be vaporised which is stored in the cavity and said substance may thus more readily be conveyed via the capillary onto the vaporiser membrane(s). In addition, the fluid stream and pressure differences caused thereby may in this manner assist in conveying the substance to be vaporised out of the cavity (cavities) onto the vaporiser membrane(s). The substance to be vaporised may partially, but preferably completely, fill the cavity or cavities.

The pressure equalisation orifice(s) is (are) preferably designed such that the substance to be vaporised, is not capable of passing through the pressure equalisation orifice(s), for example due to its surface tension, so avoiding undesired leakage of the substance to be vaporised.

In a further development, the supply orifice(s) are closed by one or more supply orifice closures and/or pressure equalisation orifice(s) are closed by one or more pressure equalisation orifice closures and are only opened immediately before consumption, for example by tearing, puncturing or displacement. In this manner, the substance to be vaporised may be protected from atmospheric influences until consumption and unwanted premature volatilisation may be prevented.

A further possible way of protecting the substance to be vaporised from atmospheric influences until consumption and preventing unwanted premature volatilisation is to subdivide the cavity (cavities) into at least one substance supply chamber and one substance storage chamber, wherein these are separated from one another by a removable partition and the substance storage chamber comprises no further orifices apart from the orifice, closed by the removable partition, to the substance supply chamber.

The described method is preferably carried out with a device according to the invention for vaporising active and/or aroma materials with the highest possible efficiency, i.e. with the highest possible ratio of active and/or aroma material input to active and/or aroma material output, comprising a preferably cylindrical hollow body, which forms or contains a flow channel, similar in dimensions to a small cigar or cigarette, preferably similar in shape and dimensions to a cigarette filter including band, comprising at least one semipermeable or permeable vaporiser membrane, which is arranged in the flow channel, for vaporising a substance containing an active and/or aroma material, wherein the substance has already been applied to the vaporiser membrane (vaporiser membrane wetted) and/or may be applied from an optionally present cavity containing the substance (see below) onto the vaporiser membrane (vaporiser membrane wettable).

The device accordingly preferably forms a mouthpiece containing an active and/or aroma material depot, which mouthpiece advantageously comprises a cylindrical sleeve, with one or more fluid inlets and one or more fluid outlets, wherein a fluid stream arises in the flow channel when the user applies suction to the air outlet (air outlets). This sleeve is in principle a holding surface for the consumer and contact area with the consumer's mouth.

In a further embodiment, the device preferably contains at least one semipermeable filter membrane for removing undesired constituents from the fluid stream. Alternatively or in addition, at least one semipermeable or permeable filter membrane may optionally be provided with an applied catalyst for breaking down undesired constituents of the fluid stream into constituents which are harmless to health.

In a further preferred development, capillaries are provided for feeding a substance to be vaporised onto the vaporiser membrane(s).

At least one cavity is preferably provided for storing one or more substance(s) to be vaporised within the device, which cavity is in connection via at least one supply orifice with the capillaries and/or vaporiser membranes and preferably contains a storage medium, for example a foam or a nonwoven fabric, in order to hinder undesired (premature) escape of the substance(s) to be vaporised, wherein prior to use the orifice(s) is (are) preferably closed by for example at least one removable supply orifice closure, in order to protect the substance(s) to be vaporised which are located in the cavity (cavities) from atmospheric influences and premature volatilisation prior to use.

As already described above, the hollow bodies and, if present, the cavities may be formed from one or more single- and/or multi-ply films.

At least one pressure equalisation orifice is furthermore preferably provided, which connects the cavity (cavities) with the flow channel and/or atmosphere, in order to assist feeding of the substance(s) to be vaporised via the capillary onto the vaporiser membrane(s), wherein the pressure equalisation orifice(s) is (are) preferably closed prior to use by at least one removable pressure equalisation orifice closure, in order to protect the substance(s) to be vaporised, which is (are) located prior to use in the cavity (cavities), from atmospheric influences and premature volatilisation.

In a further embodiment, at least one removable partition is furthermore preferably formed, which partition subdivides the cavity into at least one substance supply chamber and one substance storage chamber, wherein the substance storage chamber(s) comprises no further orifices apart from the orifice closed by the partition, and the partition is removed and/or destroyed prior to use and the substance to be vaporised accordingly flows out of the substance storage chamber(s) into the substance supply chamber(s) within the cavity.

A flange is preferably provided for connecting the device according to the invention with a further device, such as for example a heating member provided as described in WO2008/113420, wherein the air inlet (air inlets) of the flow channel is (are) in connection with the air outlets of said further device and said further device is preferably capable of supplying energy, preferably in the form of thermal energy, to a fluid stream in order optionally to assist the vaporisation process of a substance which is difficult to volatilise.

The advantages of such a method and a device based thereon are many and varied. Firstly, there is no smoke nuisance caused by combusting complex substances, such as tobacco, and secondly, no "sidestream smoke" is produced, whereby third parties are not harmed by passive smoking. Thirdly, because, in contrast with a conventional cigarette, the active and/or aroma materials and the number thereof may be selected purposefully, inhalation thereof is far less harmful to health than in the case of a normal cigarette and a carcinogenic action can be purposefully ruled out. In other words, since no combustion in the conventional sense occurs, it is possible to obtain a controlled aerosol composition without causing a nuisance to third parties.

This advantage, which is decisive for user acceptance, is achieved by the volatilisation of the active and/or aroma materials (formation of an inhalable aerosol) exclusively by a hot fluid stream, i.e. without heating, let alone combusting, the substance(s) to be vaporised by direct contact with an energy source. For the purposes of the present invention, an inhalable aerosol is here in principle a mixture of solid and/or liquid suspended particles and air. The inhalable aerosol preferably comprises a mist, i.e. a mixture mainly composed of liquid suspended particles and air, preferably as far as possible free of fine dust. The inhalable aerosol is particularly preferably a virtually pure gas mixture, i.e. a mixture of the fluid and substance, which has as far as possible been converted into the gas phase with a small proportion of liquid suspended particles.

In contrast with known methods and devices based thereon, the present method and the device based thereon offers the possibility of not only partially but rather completely delivering and even exceeding the nicotine aroma transfer which is known from a conventional cigarette and expected by consumers. Adequate nicotine aroma transfer, i.e. the quantity and intensity of inhalable nicotine and aroma per draw, is the key factor in ensuring consumer acceptance.

A further and practically important advantage of the method and a device based thereon is that the present invention may be used in combination with a heating device (which supplies energy of vaporisation to a fluid stream, such as for example a heating member according to WO 2008/113420), without the substance(s) to be vaporised coming into contact with, let alone contaminating, the heating device during use.

BRIEF DESCRIPTION OF THE FIGURES

Certain advantages and developments of the invention will now be described below with reference to the attached figures.

The reference signs used in the present document are only for illustrative purposes and should not be regarded as limiting the respective characteristics and features to the developments shown in the Figures.

a) Device according to the invention prior to use. A substance to be vaporised is located in a substance storage chamber 632, which is separated by a substance storage chamber closure 63 in the form of an adhesive seam (predetermined breaking point) from a substance supply chamber 631 filled with a storage medium 64.

b) Detail view of the substance storage chamber closure 63 in the closed state and the surrounding components with visible ply structure of the multi-ply film.

c) Device according to the invention ready for use. An additional device for heating a fluid stream is inserted into the flange 7 of the device according to the invention such that the substance storage chamber 632 is completely compressed, whereby the substance storage chamber closure 63 in the form of an adhesive seam is torn apart and all the substance to be vaporised is transferred into the substance supply chamber 631, capillary 3 and vaporiser membrane 2.

b) The inlet opening with flange 7 is facing towards the observer.

DETAILED DESCRIPTION

Figure 1:
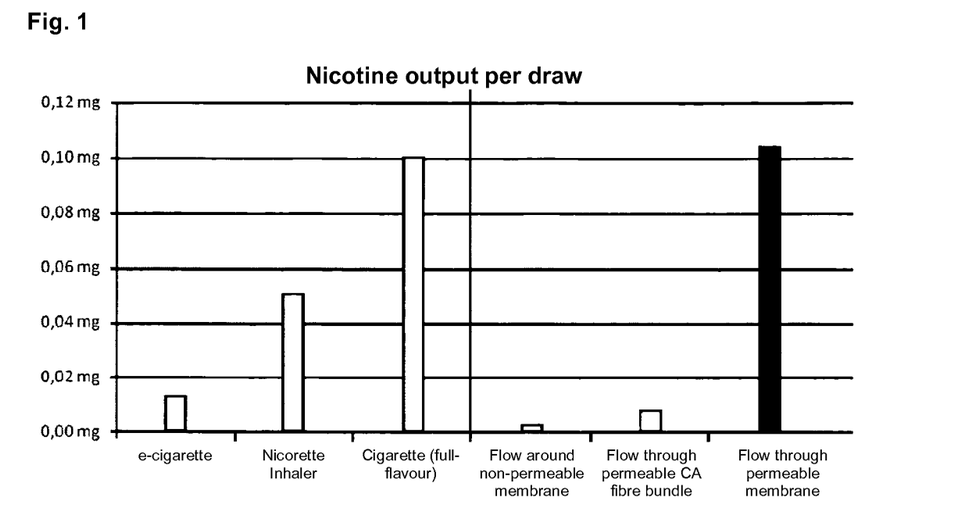
FIG. 1 shows by way of comparison the nicotine output per draw (draw volume 35 ml, duration of draw 2 s) of the e-cigarette, the Nicorette Inhaler and the conventional full-flavour cigarette on the left-hand side (available products) and, in each case impregnated with an identical quantity of substance to be vaporised, an impermeable membrane around which the fluid flows, a cellulose acetate fibre bundle (cigarette filter) through which the fluid flows and a permeable membrane 2 according to the invention made from regenerated cellulose fibre through which the fluid flows on the right-hand side (tests).
Figure 2:
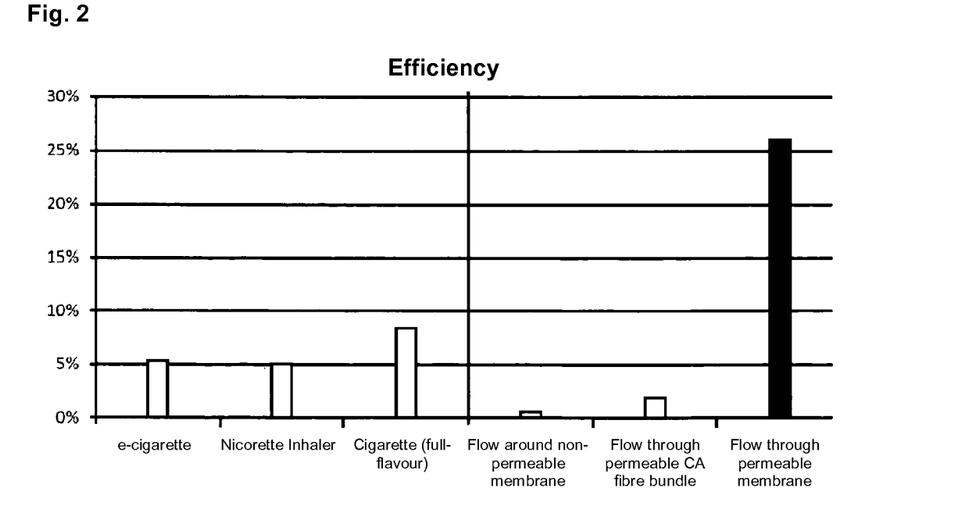
FIG. 2 shows by way of comparison the efficiency, i.e. the ratio of nicotine present in the system to that released of the e-cigarette, the Nicorette Inhaler and the conventional full-flavour cigarette on the left-hand side (available products) and, in each case impregnated with an identical quantity of substance to be vaporised, an impermeable membrane around which the fluid flows, a cellulose acetate fibre bundle (cigarette filter) through which the fluid flows and a permeable membrane 2 according to the invention made from regenerated cellulose fibre through which the fluid flows on the right-hand side (tests).
Figure 3:
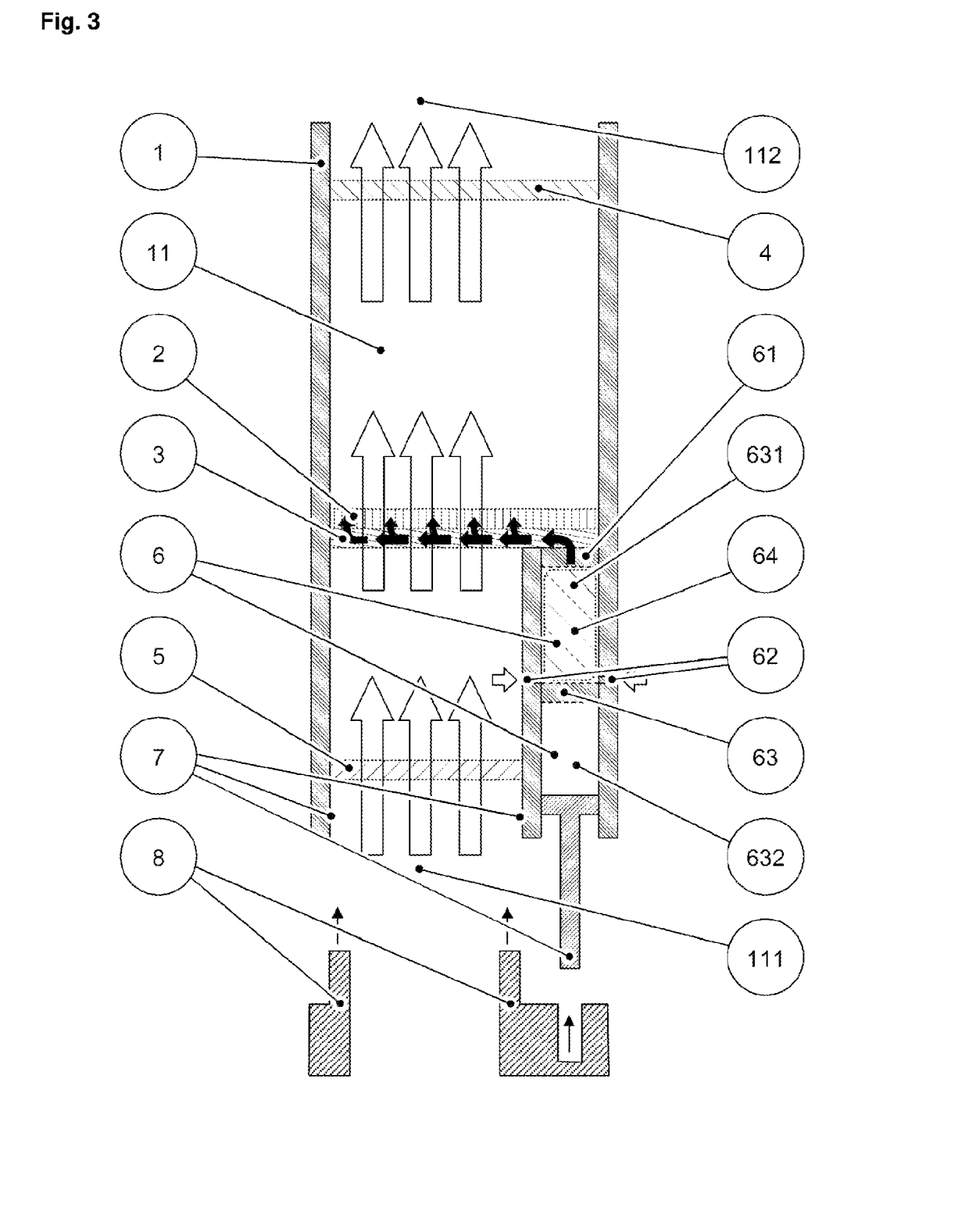
FIG. 3 shows a schematic representation of a preferred development of the method, wherein all possible constituents are listed at least once.
Figure 4:
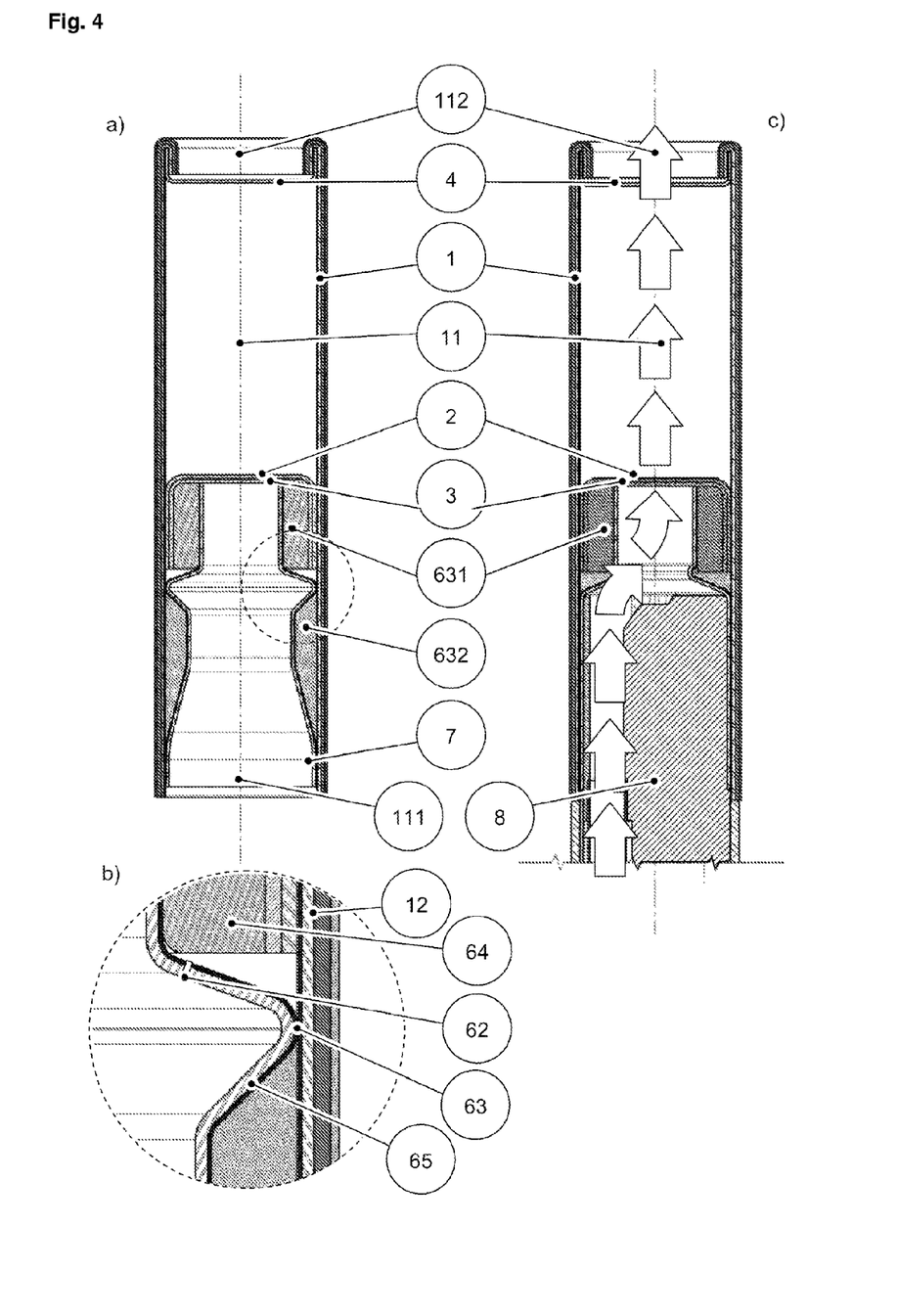
FIG. 4 shows sectional drawings of a preferred development of a device according to the invention, wherein the hollow body 1 comprises a cavity 6 with substance storage chamber 632 and substance supply chamber 631 and the hollow body 1 and cavity 6 are formed by two multi-ply films adhesively bonded to one another.
Figure 5:
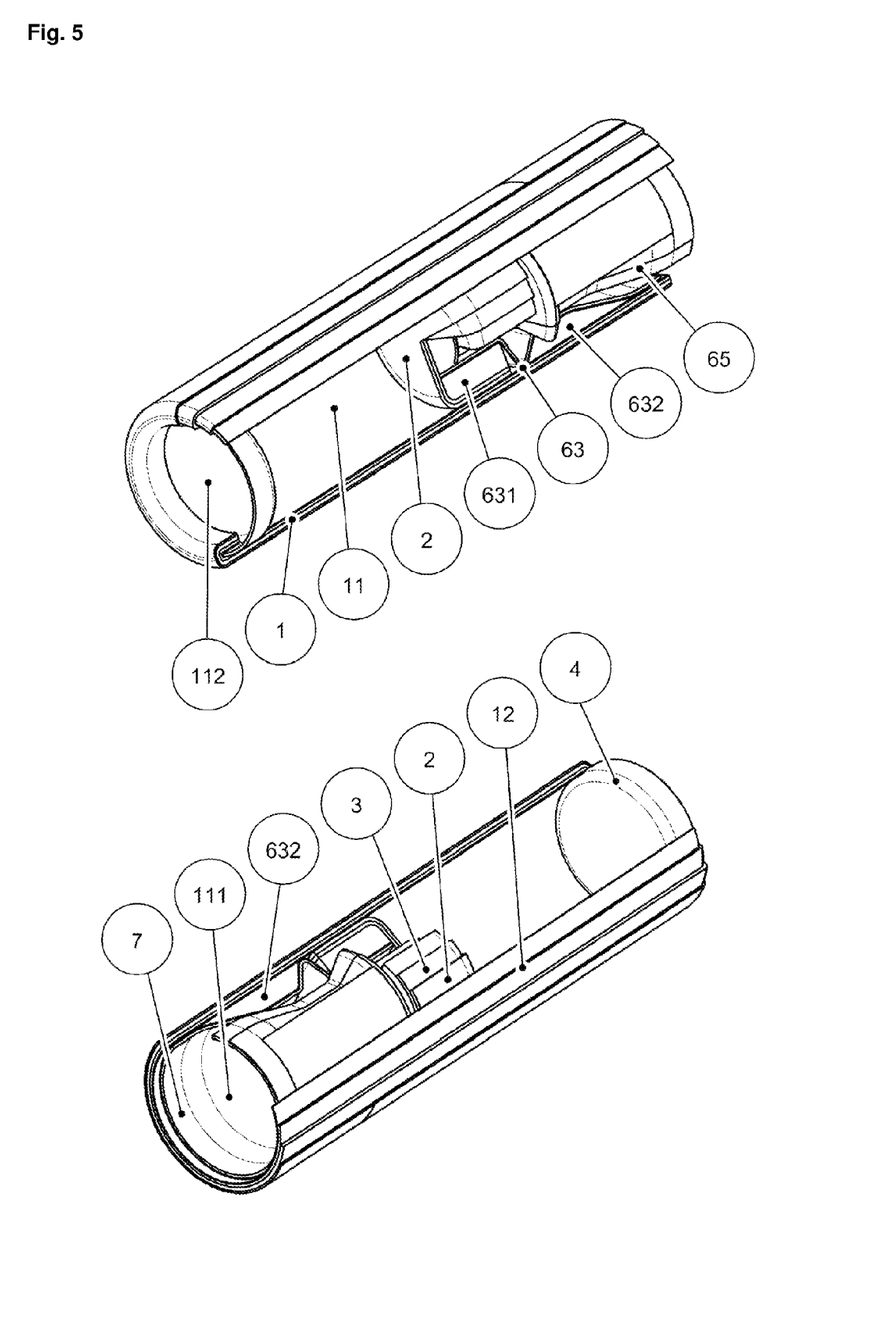
FIG. 5 shows ISO sectional views of the development of a device according to the invention from FIG. 4 a) The outlet orifice with filter membrane 4 is facing towards the observer.

In a preferred development of the invention, a device according to the invention serves as a mouthpiece for example in a device described in WO 2008/113420 A1, i.e. a device according to the invention is connected via a flange 7 with a device for release of thermal energy 8 to a fluid stream.

In this development, the device according to the invention comprises a sleeve 1 formed from a multi-ply film, preferably composed of for example PVC film, PE film, Barex film and/or aluminium foil, and paperboard and cover paper, with a fluid inlet 111 and a fluid outlet 112, a permeable vaporizer membrane 2, which is arranged in the flow channel 11, for vaporising a substance containing an active and/or aroma material, capillary 3 for feeding a substance to be vaporised onto the vaporiser membrane 2, a semipermeable filter membrane 4 downstream of the vaporiser membrane 2 for removing undesired constituents from the fluid stream, a cavity 6, arising for example by adhesively bonding a further multi-ply film with the sleeve 1, for storing a substance to be vaporised, which cavity is in connection via a supply orifice 61 with the capillaries 3 and the vaporiser membrane 2 and contains a storage medium 64 in the form of a foam, in order to hinder undesired escape of the substance to be vaporised, a plurality of pressure equalisation orifices 62, which connect the cavity 6 to the flow channel 11, in order to assist feeding of the substance(s) to be vaporised via the capillary 3 onto the vaporiser membrane 2, wherein the pressure equalisation orifices 62 are formed by microperforation of the cavity film 65, a substance storage chamber 632 within the cavity 6, which substance storage chamber is separated by a substance storage chamber closure 63 in the form of a detachable adhesive seam between the multi-ply sleeve film 12 and the multi-ply cavity film 65 from the substance supply chamber 631, which comprises the supply orifice 61, the storage medium 64 and the pressure equalisation orifices 62, and which substance storage chamber protects the substance to be vaporised from atmospheric influences and premature volatilisation prior to use.

a flange 7 for connecting the device according to the invention to a further device 8 for example a "heating member" described in WO2008/113420A1, wherein the fluid inlet 111 of the flow channel 11 is in detachable connection with the fluid outlet of said further device 8, wherein this flange 7 is designed such that when the devices are brought together the substance storage chamber 632 is completely compressed, wherein the substance storage chamber closure 63 in the form of a detachable adhesive seam tears apart and all the substance to be vaporised is transferred into the substance supply chamber 631, capillary 3 and vaporiser membrane 2.

The invention claimed is:

1. A method for volatilising active and/or aroma materials for releasing an inhalable aerosol, comprising:

flowing a fluid through a flow channel in a hollow body, the fluid in the flow channel entirely or partly flowing through at least one vaporiser membrane in a fluid stream, wherein the at least one vaporiser membrane extends laterally across the flow channel and has a thickness, taken in a longitudinal direction of the hollow body, which is less than an inner diameter of the hollow body, wherein the at least one vaporiser membrane includes a substance containing an active and/or aroma material, and wherein the fluid additionally contains thermal energy and vaporises the substance on flowing through the at least one vaporiser membrane, the fluid flowing through the at least one vaporiser membrane in a direction parallel to the longitudinal direction; and supplying the vaporised substance to the fluid stream.

2. The method according to claim 1, wherein at least one filter membrane is arranged in the flow channel, the filter membrane filtering undesired constituents out of the fluid stream and/or said constituents down into harmless products by means of a catalyst.

3. The method according to claim 2, wherein the at least one filter membrane is selected from a single-layer membrane or a multi-layer membrane, a permeable membrane or a semipermeable membrane, or combinations thereof, and is arranged orthogonally and/or at an angle to the fluid stream.

4. The method according to claim 1, wherein the at least one vaporiser membrane is wetted with a substance to be vaporised by means of capillary action, wherein capillaries are in contact with the at least one vaporiser membrane and/or are contained therein, and wherein the at least one vaporiser membrane and/or capillaries furthermore come into contact with the substance to be vaporised.

5. The method according to claim 4, wherein the substance to be vaporised which is in contact with the at least one vaporiser membrane and/or capillaries is located in a cavity or a plurality of cavities, wherein the cavity or cavities has one or more supply orifices through which the at least one vaporiser membrane and/or capillaries are in connection with the substance to be vaporised.

6. The method according to claim 5, wherein the cavity or cavities comprises at least one further orifice for pressure equalisation, which is in contact with the flow channel within the hollow body and/or with atmospheric pressure outside the hollow body and through which the substance to be vaporised cannot pass, wherein the substance to be vaporised at least partially fills the cavity or cavities.

7. The method according to claim 5, wherein one or more removable closures are located between the cavity or cavities and the flow channel and/or the capillaries and/or the at least one vaporiser membrane.

8. The method according to claim 6, wherein one or more removable closures are located between the cavity or cavities and the flow channel and/or the capillaries and/or the at least one vaporiser membrane.

9. The method according to claim 8, wherein the cavity or cavities are subdivided by a removable partition into a substance supply chamber and a substance storage chamber.

10. The method according to claim 9, wherein the cavity or cavities contain at least one storage medium configured to store the substance to be vaporised, wherein the at least one storage medium is a foam or a nonwoven fabric.

11. A device for volatilising active and/or aroma materials for releasing an inhalable aerosol, comprising:
    a hollow body in which is formed a flow channel; and
    at least one vaporiser membrane arranged in the flow channel, the at least one vaporiser membrane extending laterally across the flow channel and having a thickness, taken in a longitudinal direction of the hollow body, which is less than an inner diameter of the hollow body,
    wherein the at least one vaporiser membrane includes a substance containing an active and/or aroma material,
    wherein the substance is vaporisable by a fluid passing through the at least one vaporiser membrane in a fluid stream, and
    wherein the at least one vaporiser membrane is configured such that the fluid passes therethrough in a direction parallel to the longitudinal direction.

12. The device according to claim 11, wherein the hollow body is cylindrical.

13. The device according to claim 12, further comprising at least one filter membrane arranged in the flow channel configured to filter out undesired constituents from the fluid stream, wherein the at least one filter membrane comprising a catalyst configured to break down the undesired constituents into harmless products.

14. The device according to claim 13, wherein the at least one filter membrane is selected from a single-layer membrane or a multi-layer membrane, a permeable membrane or a semipermeable membrane, or combinations thereof, and is arranged orthogonally and/or at an angle to the fluid stream.

15. The device according to claim 12, further comprising one or more cavities at least partially filled with a vaporisable substance, wherein the vaporisable substance is in contact, directly and/or via capillaries, with the at least one vaporiser membrane through one or more supply orifices.

16. The device according to claim 15, wherein the one or more cavities comprise at least one further orifice for pressure equalisation, which is in contact with the flow channel within the hollow body and/or with atmospheric pressure outside the hollow body, and is configured such that the vaporisable substance cannot pass therethrough.

17. The device according to claim 15, wherein the hollow body and the one or more cavities are formed from one or more single-ply films and/or multi-ply films.

18. The device according to claim 14, wherein one or more removable closures is located between a cavity or cavities and the flow channel and/or the capillaries and/or the at least one vaporiser membrane, or the cavity or cavities are subdivided by a removable partition into a substance supply chamber and a substance storage chamber.

19. The device according to claim 13, wherein the at least one vaporiser membrane and/or the at least one filter membrane comprise a laid fabric, a nonwoven fabric, a woven fabric, a warp knitted fabric, and/or a weft knitted fabric.

20. A method for volatilising active and/or aroma materials for releasing an inhalable aerosol, comprising:
    flowing a fluid through a flow channel in a hollow body, the fluid in the flow channel entirely or partly flowing through at least one vaporiser membrane in a fluid stream,
        wherein the at least one vaporiser membrane comprises a two-dimensional structure,
        wherein the at least one vaporiser membrane has been and/or is wetted with a substance containing an active and/or aroma material, and
        wherein the fluid additionally contains thermal energy and vaporises the substance on flowing through the at least one vaporiser membrane, the fluid flowing through the at least one vaporiser membrane in a direction parallel to a longitudinal direction of the hollow body; and
    supplying the vaporised substance to the fluid stream.

21. The method according to claim 20, wherein the two-dimensional structure extends with major dimensions laterally across the flow channel and extends with a minor dimension in a thickness direction perpendicular to the longitudinal direction.

* * * * *